(12) United States Patent
Sawa et al.

(10) Patent No.: US 7,172,576 B2
(45) Date of Patent: Feb. 6, 2007

(54) MEDICINAL-LIQUID INJECTION APPARATUS

(75) Inventors: Yoshiki Sawa, Nishinomiya (JP); Satoshi Taketani, Osaka (JP); Shinji Ozawa, Nagoya (JP); Manabu Shimogami, Seto (JP)

(73) Assignee: Asahi Intecc Co., Ltd., Nagoya (JP)

( * ) Notice: Subject to any disclaimer, the term of this patent is extended or adjusted under 35 U.S.C. 154(b) by 0 days.

(21) Appl. No.: 11/242,482

(22) Filed: Oct. 3, 2005

(65) Prior Publication Data
US 2006/0025720 A1    Feb. 2, 2006

Related U.S. Application Data

(63) Continuation of application No. PCT/JP04/05968, filed on May 6, 2004.

(30) Foreign Application Priority Data

May 6, 2003    (JP) ............................. 2003-128105

(51) Int. Cl.
*A61M 5/178* (2006.01)
(52) U.S. Cl. ................................. 604/164.01
(58) Field of Classification Search ........... 604/165.01, 604/164.01, 264
See application file for complete search history.

(56) References Cited

U.S. PATENT DOCUMENTS

| | | | |
|---|---|---|---|
| 3,833,003 A | 9/1974 | Taricco | |
| 4,578,061 A | 3/1986 | Lemelson | |
| 5,190,528 A | 3/1993 | Fonger et al. | |
| 5,232,456 A | 8/1993 | Gonzalez | |
| 5,261,889 A | 11/1993 | Laine et al. | |
| 5,354,279 A | 10/1994 | Höfling | |
| 5,419,777 A | 5/1995 | Höfling | |
| 5,464,395 A | 11/1995 | Faxon et al. | |
| 5,478,313 A | 12/1995 | White | |
| 5,573,513 A | 11/1996 | Wozencroft | |
| 5,578,014 A | 11/1996 | Erez et al. | |

(Continued)

FOREIGN PATENT DOCUMENTS

JP    60-160808 U1    10/1985

(Continued)

OTHER PUBLICATIONS

U.S. Appl. No. 11/122,733, filed May 5, 2005, Katoh et al.

*Primary Examiner*—Nicholas D. Lucchesi
*Assistant Examiner*—Laura A. Bouchelle
(74) *Attorney, Agent, or Firm*—Burr & Brown (57) ABSTRACT

It is a purpose to provide a medicinal-liquid injection apparatus in which a needle-like tubular member is smoothly movable in a lumen without damaging an inner circumferential surface of the lumen. It includes that the needle-like tubular member having an acuminate needle portion as a free end portion thereof, in which a medicinal liquid can flow, is inserted in the lumen of a tubular main body insertable in a body of a living being, and a protection member having a flexible portion provided in a state such that the protection member is movable together with the needle-like tubular member and such that the flexible portion is interposed between an inner circumferential surface of the lumen and a tip of the needle portion of the needle-like tubular member.

10 Claims, 7 Drawing Sheets

U.S. PATENT DOCUMENTS

| | | |
|---|---|---|
| 5,681,292 A | 10/1997 | Tober et al. |
| 5,702,384 A | 12/1997 | Umeyama et al. |
| 5,843,034 A | 12/1998 | Redfern et al. |
| 5,906,594 A * | 5/1999 | Scarfone et al. ....... 604/165.01 |
| 5,921,971 A * | 7/1999 | Agro et al. ................. 604/523 |
| 6,068,638 A | 5/2000 | Makower |
| 6,217,554 B1 | 4/2001 | Green |
| 6,283,947 B1 | 9/2001 | Mirzaee |
| 6,368,303 B1 | 4/2002 | Caizza |
| 6,375,615 B1 | 4/2002 | Flaherty et al. |
| 6,461,296 B1 | 10/2002 | Desai |
| 6,517,516 B1 | 2/2003 | Caizza |
| 6,544,230 B1 | 4/2003 | Flaherty et al. |
| 6,547,767 B1 | 4/2003 | Moein |
| 6,689,099 B2 | 2/2004 | Mirzaee |
| 6,692,466 B1 | 2/2004 | Chow et al. |
| 6,706,017 B1 | 3/2004 | Dulguerov |
| 2002/0072706 A1 | 6/2002 | Hiblar et al. |
| 2003/0040712 A1 | 2/2003 | Ray et al. |
| 2003/0171714 A1 | 9/2003 | Katoh et al. |
| 2004/0176726 A1 | 9/2004 | Katoh et al. |
| 2005/0004522 A1 | 1/2005 | Katoh et al. |

FOREIGN PATENT DOCUMENTS

| | | |
|---|---|---|
| JP | 06-032655 B2 | 5/1994 |
| JP | 06-086744 U1 | 12/1994 |
| JP | 10-328302 A1 | 12/1998 |
| JP | 2001-104487 A1 | 4/2001 |
| JP | 2001-299927 A1 | 10/2001 |
| JP | 2001-314514 A1 | 11/2001 |
| JP | 2002-306606 A1 | 10/2002 |
| JP | 2002306606 A * | 10/2002 |
| JP | 2003-339874 A1 | 12/2003 |
| WO | WO 92/10142 A1 | 6/1992 |
| WO | WO 00/67647 A1 | 11/2000 |
| WO | WO 01/49357 A2 | 7/2001 |

* cited by examiner

MEDICINAL-LIQUID INJECTION APPARATUS

This application is a continuation of the International Application PCT/JP2004/005968, filed May 6, 2004, which claims the benefit under 35 U.S.C. § 119(a)–(d) of Japanese Application 2003-128105, filed May 6, 2003, the entireties of which are incorporated herein by reference.

TECHNICAL FIELD

The present invention relates to a structure of a medicinal-liquid injection apparatus that injects an appropriate medicinal liquid to, e.g., a lesion of a tissue of an internal body of a living being.

BACKGROUND ART

Conventionally various treatments, examinations, and procedures have been carried out by inserting a medical instrument such as a catheter into a tubular organ of a human body such as a blood vessel, a digestive tract, or a urinary duct. In addition, recently a medicinal-liquid injection apparatus such as a medicinal-liquid injection catheter has been used to carry out a treatment or a procedure of injecting an appropriate medicinal liquid to a lesion of a body tissue of a living being (see, e.g., Patent Documents 1 and 2).

As is well known in the art, the medicinal-liquid injection catheter includes a tubular main body having a lumen therein, and a needle-like tubular member that is constituted by a thin tube in which a medicinal liquid can flow, that includes an acuminate needle portion as a free end portion thereof, and that is inserted in the lumen so as to be movable in an axial direction of the main body. The main body of the medicinal-liquid injection catheter is inserted in a blood vessel so as to reach a lesion of a body tissue, and therein the needle-like tubular member is moved in a lengthwise direction thereof. Thus, through a hole formed in an end opening portion or a tubular wall of the catheter main body, the needle portion as the free end portion of the needle-like tubular member is caused to project out of the lumen into an outside space, so as to puncture the lesion of the body tissue. In this state, the medicinal liquid is injected to the lesion through the needle-like tubular member.

Meanwhile, when the catheter main body of the medicinal-liquid injection catheter is inserted in, e.g., the blood vessel as described above, some portions of the catheter main body are bent or curved in the winding blood vessel. Therefore, when the needle-like tubular member is inserted in the lumen of the catheter main body and is moved in the axial direction of the catheter main body, the tip of the needle portion of the needle-like tubular member may contact an inner circumferential surface of the lumen to be lodged therein. In this case, the needle-like tubular member may not be moved smoothly in the lumen, and also the inner surface of the lumen may be damaged.

Generally, the needle-like tubular member is long, and the lumen of the main body has an inner diameter greater than an outer diameter of the needle-like tubular member by a certain amount so as to allow the needle-like tubular member to be sufficiently inserted therein. Thus, in the conventional medicinal-liquid injection apparatus such as the medicinal-liquid injection catheter, the needle-like tubular member may be deflected when the needle-like tubular member is moved in the lumen, therefore it is difficult to cause the needle portion of the needle-like tubular member to project stably in a desired direction out of the hole through which the lumen opens outward.

Patent Document 1: Japanese Patent Application Publication No. 2001-104487
Patent Document 2: Japanese Patent Application Publication No. 2001-299927

DISCLOSURE OF THE INVENTION

PROBLEM TO BE SOLVED BY THE INVENTION

The present invention has been developed in the above-explained background. The present invention provides a novel structure that can advantageously assure that a needle-like tubular member including a needle portion as a free end portion thereof is moved smoothly in a lumen, and that can prevent an inner circumferential surface of the lumen from being damaged when the needle-like tubular member is moved in the lumen. In addition, the present invention provides a medicinal-liquid injection apparatus that can cause a needle portion of a needle-like tubular member to project stably in a desired direction out of a hole through which a lumen opens outward.

MEANS FOR SOLVING THE PROBLEM

In the present invention, a first mode to solve the above problem is a medicinal-liquid injection apparatus characterized by including (a) a tubular main body which is constituted by a tubular body insertable in a body of a living being and which has a lumen therein; (b) a projection hole which is constituted by a hole provided in the tubular main body and through which the lumen opens outward; (c) a needle-like tubular member which includes an acuminate needle portion as a free end portion thereof, which is constituted by a thin tube interiorly supplied with a predetermined medicinal liquid, and which is inserted in the lumen of the tubular main body such that the needle-like tubular member is movable in an axial direction of the tubular main body and the needle portion is caused to project outward through the projection hole of the tubular main body; and (d) a protection member which includes a flexible portion being at least partly flexible, which is provided in the lumen such that the protection member is movable together with the needle-like tubular member and such that the flexible portion is interposed between an inner circumferential surface of the lumen and a tip of the needle portion of the needle-like tubular member, wherein when the needle portion of the needle-like tubular member is caused to project out of the projection hole of the tubular main body so as to puncture a tissue of the body of the living being in a state in which the tubular main body is inserted and located in the body of the living being, the medicinal liquid supplied through the needle-like tubular member is injected to the tissue of the body.

In the medicinal-liquid injection apparatus according to a second mode of the present invention, the flexible portion of the protection member is at least partly formed of a radiopaque material.

In the medicinal-liquid injection apparatus according to a third mode of the present invention, a marker member formed of a radiopaque material is provided at a fixed position in a vicinity of the projection hole of the tubular main body.

In the medicinal-liquid injection apparatus according to a fourth mode of the present invention, a portion of the lumen that is located in a vicinity of the projection hole is constituted by a narrowed portion which is narrower than a diameter of the lumen.

In the medicinal-liquid injection apparatus according to a fifth mode of the present invention, the needle-like tubular member is connected to a medicinal-liquid supply device which supplies the predetermined medicinal liquid into the needle-like tubular member.

In the medicinal-liquid injection apparatus according to a sixth mode of the present invention, the protection member includes a support portion which is supported by the needle-like tubular member such that the support portion is integrally movable with the needle-like tubular member, and the flexible portion which is integral with the support portion and which externally surrounds the tip of the needle portion of the needle-like tubular member and is thus interposed between the inner circumferential surface of the lumen and the tip of the needle portion.

In the medicinal-liquid injection apparatus according to a seventh mode of the present invention, the protection member further includes, as an integral portion thereof, an expansible and compressible portion having an expansibility and a compressibility, wherein in accordance with a retraction of the expansible and compressible portion, the flexible portion of the protection member is displaced relative to the needle-like tubular member, so that the tip of the needle portion of the needle-like tubular member is exposed out of the surrounding of the flexible portion, and wherein the lumen includes, in a vicinity of the projection hole, an engaging portion that engages, when the needle-like tubular member is moved in a direction to cause the needle portion to project out of the projection hole, the protection member, so as to prevent the protection member from projecting out of the projection hole, and causes the expansible and compressible portion to be compressed.

In the medicinal-liquid injection apparatus according to an eighth mode of the present invention, the protection member is constituted by a coil formed by winding a wire, and the coil includes a first spring portion that has a great pitch and is expansible and compressible, and a second spring portion that has a small pitch, and wherein the expansible and compressible portion is constituted by the first spring portion of the coil and the flexible portion is constituted by the second spring portion of the coil.

In the medicinal-liquid injection apparatus according to a ninth mode of the present invention, the engaging portion provided in the vicinity of the projection hole in the lumen is constituted by a narrowed portion formed by narrowing a portion of the lumen located in the vicinity of the projection hole.

In the medicinal-liquid injection apparatus according to a tenth mode of the present invention, the protection member includes an insertion portion which is inserted in an inner hole of the needle-like tubular member and is longer than the needle-like tubular member, and the flexible portion which is integral with an end of the insertion portion and which projects, in a state in which the insertion portion is inserted in the inner hole of the needle-like tubular member, out of an opening of the tip of the needle portion of the needle-like tubular member, so that the flexible portion is interposed between the inner circumferential surface of the lumen and the tip of the needle portion.

In the medicinal-liquid injection apparatus according to an eleventh mode of the present invention, the insertion portion of the protection member is constituted by a long wire.

In the medicinal-liquid injection apparatus according to a twelfth mode of the present invention, the flexible portion of the protection member is constituted by a coil spring which is fixed to the insertion portion.

In the medicinal-liquid injection apparatus according to a thirteenth mode of the present invention, the projection hole is formed in a tubular wall of the tubular main body, such that the projection hole opens in a direction perpendicular to the axial direction of the tubular main body, and the inner circumferential surface of the lumen includes a guide surface which guides, when the needle-like tubular member is moved in the axial direction and the needle portion of the needle-like tubular member slides on the guide surface, the needle portion toward the projection hole, and which is formed to have a convexly curved shape which is curved toward the direction in which the projection hole opens, as seen in a forward direction in which the tubular main body is inserted in the body of the living being.

In the medicinal-liquid injection apparatus according to a fourteenth mode of the present invention, the needle portion of the needle-like tubular member has a curved shape corresponding to the guide surface interiorly formed in the tubular main body and having the convexly curved shape, and wherein the convexly curved shape of the guide surface and the curved shape of the needle portion cooperate with each other to cause the needle portion of the needle-like tubular member to project out of the projection hole, toward a direction approximating the direction perpendicular to the axial direction of the tubular main body.

The above problem has been solved by a fifteenth mode of the present invention according to which there is provided a medicinal-liquid injection apparatus characterized by including (a) a tubular main body which is constituted by a tubular body insertable in a body of a living being and which has a lumen therein; (b) a projection hole which is constituted by a hole provided in the tubular main body so as to allow the lumen to open outward, and which has, in one direction perpendicular to an axial direction of the tubular main body, a width smaller than a width of the lumen in the one direction; (c) a needle-like tubular member which includes an acuminate needle portion, as a free end portion thereof, which is constituted by a thin tube interiorly supplied with a predetermined medicinal liquid, and which is inserted in the lumen of the tubular main body such that the needle-like tubular member is movable in the axial direction and the needle portion is caused to project outward through the projection hole; and (d) a leading surface which is provided in an inner circumferential surface of the lumen of the tubular main body, and which guides the needle portion toward the projection hole when the needle-like tubular member is moved in the axial direction and the needle portion of the needle-like tubular member slides on the guide surface, wherein when the needle portion of the needle-like tubular member is caused to project out of the projection hole of the tubular main body so as to puncture a tissue of the body of the living being in a state in which the tubular main body is inserted and located in the body of the living being, the medicinal liquid supplied through the needle-like tubular member is injected to the tissue of the body.

ADVANTAGEOUS EFFECT OF THE INVENTION

In the medicinal-liquid injection apparatus according to the first mode of the present invention, the flexible portion of the protection member is interposed between the tip of the needle portion of the needle-like tubular member and the inner circumferential surface of the lumen. Therefore, when the needle-like tubular member is moved in the lumen, the flexible portion of the protection member may contact the inner surface of the lumen, but the tip of the needle portion can be advantageously avoided from contacting the inner surface of the lumen. Thus, when the needle-like tubular member is inserted, and is moved in the axial direction, in the lumen of the tubular main body, inserted in, e.g., a winding portion of the body of the living being, the tip of the needle portion can be prevented from being caught by the inner surface of the lumen.

Thus, the medicinal-liquid injection apparatus according to the present invention can effectively assure that the needle-like tubular member is smoothly moved in the lumen and can advantageously prevent the inner surface of the lumen from being damaged when the needle-like tubular member is moved in the lumen. Consequently an operation using the medicinal-liquid injection apparatus can be smoothly carried out, and the favorable operating condition of the medicinal-liquid injection apparatus can be stably assured.

In the medicinal-liquid injection apparatus according to the second mode of the present invention, when the needle-like tubular member is inserted, and is moved in the axial direction, in the lumen of the tubular main body, a position of the flexible portion interposed between the tip of the needle portion of the needle-like tubular member and the inner circumferential surface of the lumen can be observed by radioscopy. Since the position of the flexible portion can be observed, a position of the needle portion of the needle-like tubular member in the lumen can be easily recognized. Consequently the operation using the medicinal-liquid injection apparatus can be more smoothly carried out.

In the medicinal-liquid injection apparatus according to the third mode of the present invention, when the tubular main body is inserted in the body of the living being, a position of the marker member can be observed by radioscopy. Since the position of the marker member can be observed, a position of the tubular main body in the body of the living being can be easily recognized. Consequently the operation using the medicinal-liquid injection apparatus can be more smoothly carried out.

In the medicinal-liquid injection apparatus according to the fourth mode of the present invention, the needle portion of the needle-like tubular member can be caused to project stably from the lumen via the projection hole toward the desired direction.

In the medicinal-liquid injection apparatus according to the fifth mode of the present invention, the predetermined medicinal liquid can be reliably injected, through the needle-like tubular member, to the tissue of the body of the living being.

In the medicinal-liquid injection apparatus according to the sixth mode of the present invention, the flexible portion of the protection member can be reliably moved together with the needle-like tubular member, in the lumen, such that the flexible portion of the protection member is interposed between the inner circumferential surface of the lumen and the tip of the needle portion of the needle-like tubular member. In addition, when the needle-like tubular member is moved in the lumen, the tip of the needle portion of the needle-like tubular member can be effectively prevented from being contacted with, and caught by, the inner surface of the lumen.

In the medicinal-liquid injection apparatus according to the seventh mode of the present invention, when the needle-like tubular member is moved in the lumen so that the needle portion of the needle-like tubular member is caused to project out of the projection hole, the engaging portion engages the protection member so as to inhibit the protection member from projecting out of the projection hole, and causes the expansible and compressible portion of the protection member to be compressed. Therefore, in the medicinal-liquid injection apparatus, when the needle-like tubular member is moved in the lumen, only the needle-like tubular member is caused to project out of the projection hole. Thus, the needle portion of the needle-like tubular member can be reliably caused to puncture the body tissue of the living being without being interfered with by the protection member.

In the medicinal-liquid injection apparatus according to the eighth mode of the present invention, the protection member can enjoy a considerably simple structure. Consequently the needle portion of the needle-like tubular member and the inner circumferential surface of the lumen can be protected without needing to complicate the structure of the medicinal-liquid injection apparatus. In addition, it is effectively assured that the needle-like tubular member can be smoothly moved in the lumen.

In the medicinal-liquid injection apparatus according to the ninth mode of the present invention, the engaging portion can be formed in the lumen so as to have a simple structure.

In the medicinal-liquid injection apparatus according to the tenth mode of the present invention, the tip of the needle-like tubular member is protected while a rigidity of the needle-like tubular member is increased. Therefore, the needle-like tubular member can be easily inserted in the tubular main body, and moved along a central axis line of the main body, while the inner surface of the tubular main body is not damaged by the tip of the needle-like tubular member. In addition, the protection member can enjoy a considerably simple structure. Consequently the needle portion of the needle-like tubular member and the inner circumferential surface of the lumen can be protected without needing to complicate the structure of the medicinal-liquid injection apparatus. In addition, it is effectively assured that the needle-like tubular member can be smoothly moved in the lumen.

In the medicinal-liquid injection apparatus according to the eleventh mode of the present invention, since the insertion portion constituted by the long wire is inserted in the lumen, the rigidity of the needle-like tubular member is more advantageously increased. Consequently the needle-like tubular member can enjoy an advantageously increased pushability into the lumen.

In the medicinal-liquid injection apparatus according to the twelfth mode of the present invention, the flexible portion of the protection member can enjoy a simpler structure.

In the medicinal-liquid injection apparatus according to the thirteenth mode of the present invention, the needle portion can be more smoothly caused to project from the lumen of the tubular main body. Therefore, the operation using the medicinal-liquid injection apparatus can be more smoothly carried out.

In the medicinal-liquid injection apparatus according to the fourteenth mode of the present invention, when the needle portion of the needle-like tubular member is caused to project out of the projection hole of the tubular main body, the needle portion can be projected so as to be located in the vicinity of the projection hole. Thus, a position of the tip of the needle-like tubular member can be more easily recognized from the position of the projection hole. In addition, since the needle portion projects out of the projection hole, in a direction nearer to a direction perpendicular to the axial direction of the tubular main body, the needle portion can puncture a desirable portion of the body tissue, with a greater component force acting in the direction perpendicular to the axial direction of the tubular main body. Therefore, the needle portion can be more smoothly caused to advance to the desirable portion of the body tissue.

In the medicinal-liquid injection apparatus according to the fifteenth mode of the present invention, when the needle-like tubular member is moved in the lumen of the tubular main body, the needle portion of the needle-like tubular member is smoothly guided by the leading surface so as to project out of the projection hole whose width is narrowed in one direction perpendicular to the axial direction of the tubular main body. Thus, when the needle portion projects out of the projection hole, the needle portion can be advantageously prevented from being "deflected" in the one direction perpendicular to the axial direction of the tubular main body.

In the medicinal-liquid injection apparatus according to the present invention, the needle portion of the needle-like tubular member can be stably caused to project out of the projection hole of the tubular main body, toward a desirable direction. Consequently the needle portion can be reliably caused to advance to a desirable portion of the body tissue. Therefore, the operation using the medicinal-liquid injection apparatus can be smoothly carried out. In addition, the ease of use of the medicinal-liquid injection apparatus can be effectively assured.

EXPLANATION OF REFERENCE NUMERALS

10 catheter main body
12 lumen
14 needle portion
16 needle-like tubular member
20 projection hole
28 guide surface
30 leading surface
36 syringe
46 strand portion
42, 64 protection member
52 second spring portion
54 first spring portion
62 cardiac muscle
66 insertion portion
68 flexible portion

BEST MODE FOR CARRYING OUT THE INVENTION

Hereinafter, to more concretely explain the present invention, there will be described in detail a structure of a medicinal-liquid injection apparatus as an embodiment of the present invention, by reference to the drawings.

Figure 1:
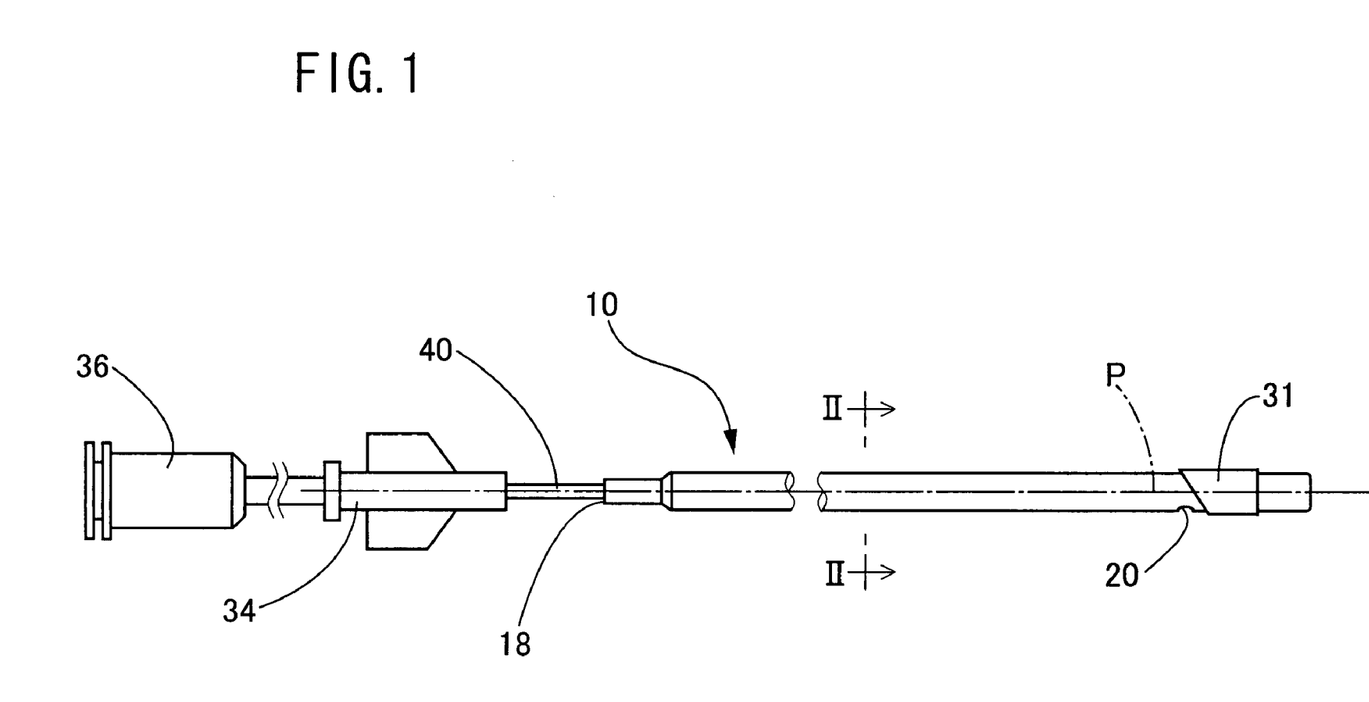
FIG. 1 is a front explanatory view of an example of a medicinal-liquid injection catheter having a structure in accordance with the present invention.
Figure 2:
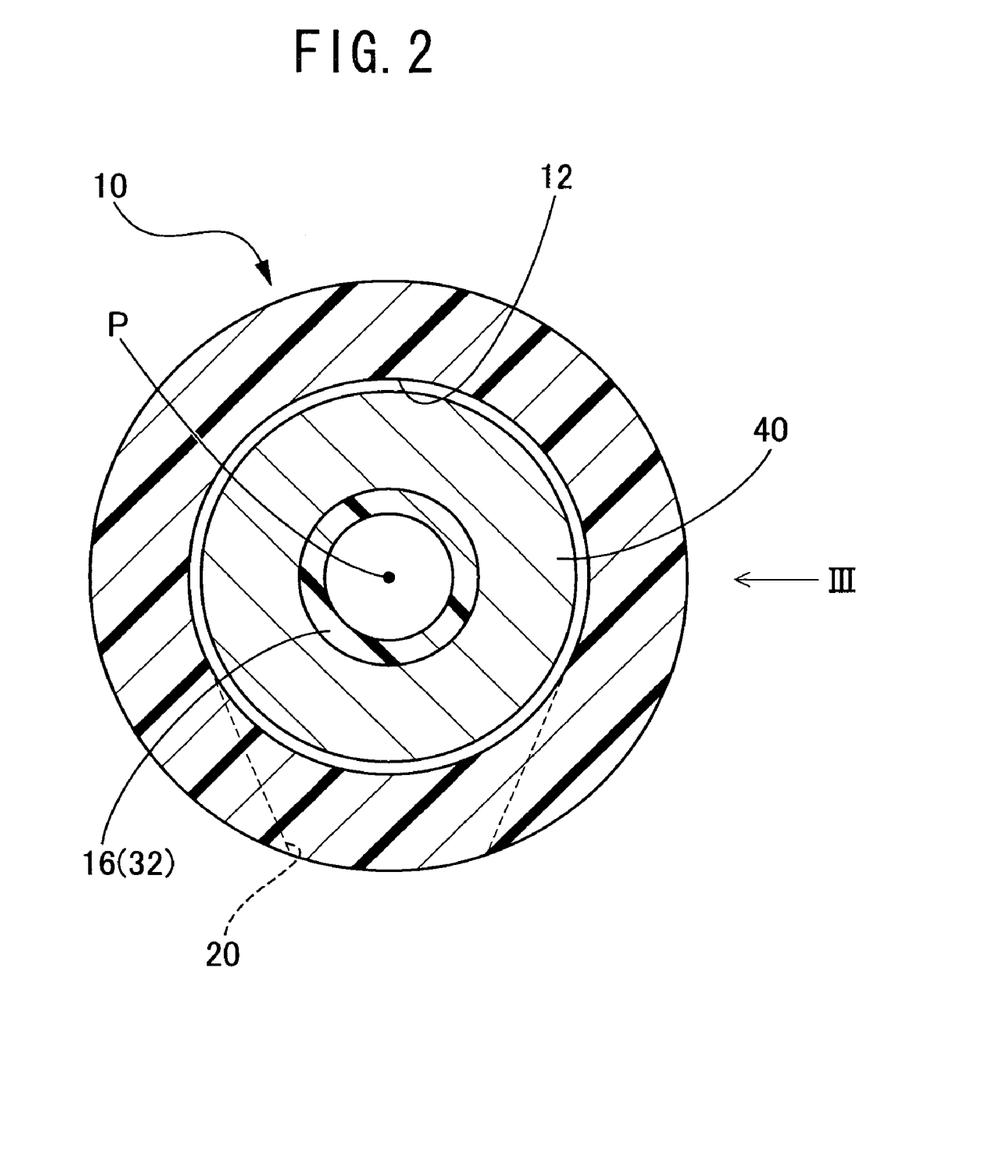
FIG. 2 is an enlarged cross-sectional explanatory view taken along line II—II of FIG. 1.
Figure 3:
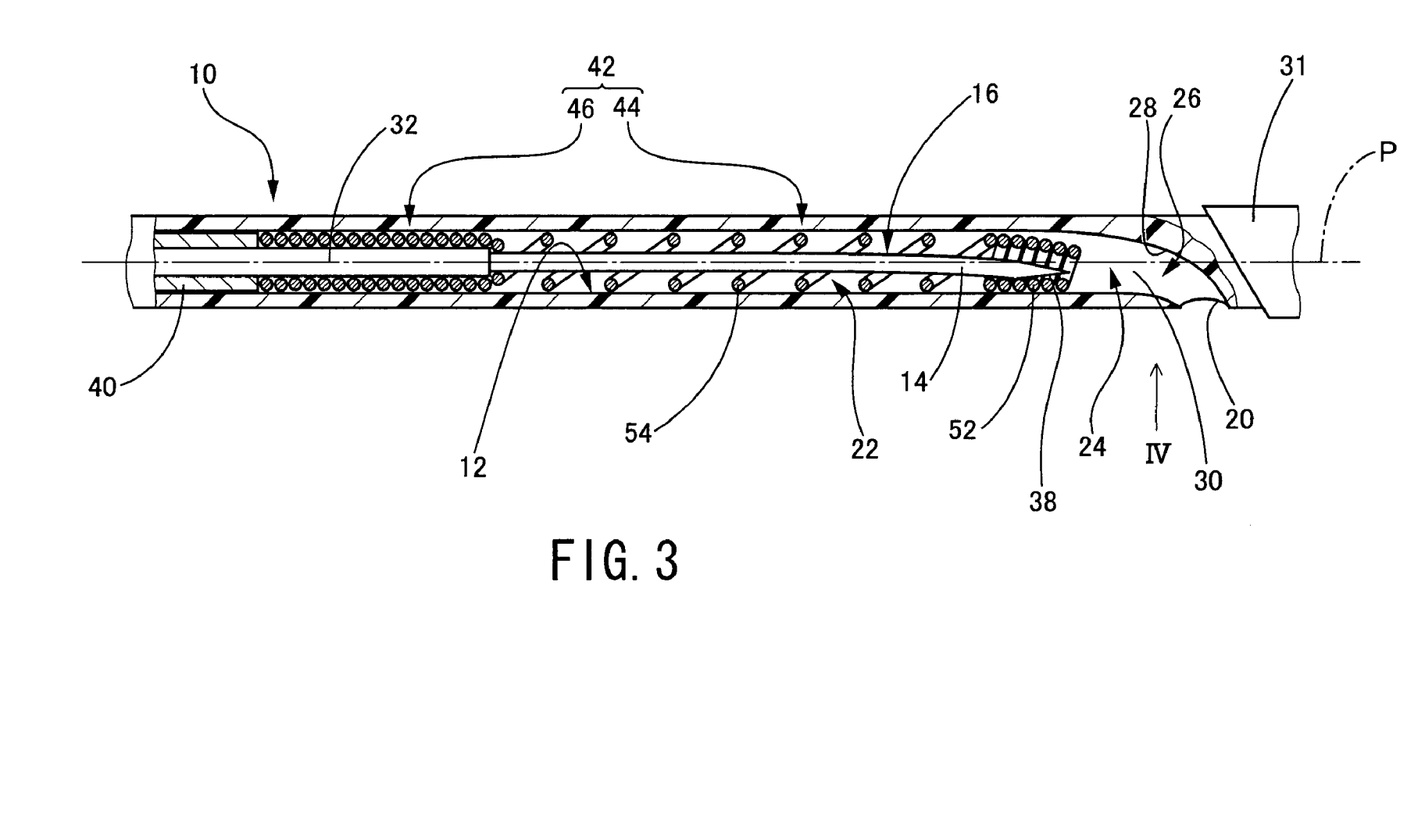
FIG. 3 is a partly cross-sectional explanatory view taken along arrow III in FIG. 2.

FIGS. 1 to 3 show a front view of a medicinal-liquid injection catheter which is an embodiment of a medicinal-liquid injections apparatus having a structure in accordance with the present invention and is used to inject a medicinal liquid to a lesion of cardiac muscle; and show two sorts of cross-section views of the injection catheter, respectively, that are viewed in different directions. In those figures, reference numeral 10 designates a catheter main body that is constituted by a long tubular body and functions as a tubular main body. The catheter main body 10 interiorly has a lumen 12 that is coaxial with a central axis P of the catheter main body 10, and continuously extends in an axial direction (leftward and rightward directions in FIG. 1) of the catheter main body 10. In the lumen 12 of the catheter main body 10, there is provided a needle-like tubular member 16 including an acuminate needle portion 14 as a free end portion thereof, such that the needle-like tubular member 16 is movable in the axial direction of the catheter main body 10.

More specifically described, the catheter main body 10 has a thickness and a length that assure that an entire length of the catheter main body 10 can be inserted in a blood vessel extending from a femoral portion, or a wrist portion, of a human body to the heart of the same. The catheter main body 10 is constituted by cylindrical inner and outer layers each of which has a flexibility and is formed of an appropriate resin, and a stainless steel wire that is embedded between the two layers. Thus, the catheter main body 10 can enjoy appropriate rigidity and flexibility that are well balanced, and accordingly it can be smoothly inserted in a winding blood vessel. However, the materials used to form the catheter main body 10 are by no means limited to any specific ones, and materials having a desirable elasticity, e.g., a synthetic resin such as polyamide, a superelastic alloy such as Ni—Ti alloy, a metal such as stainless steel, etc. can be used, if appropriate, in place of the above-described materials.

The catheter main body 10 has a rear-end opening 18 in an end portion thereof (hereinafter, referred to as the rear end portion) located in a rear portion thereof (a left-hand portion in FIG. 1) in an insertion direction in which the catheter main body 10 is inserted in the blood vessel. The lumen 12 formed in the catheter main body 10 opens rearward through the rear-end opening 18.

In addition, the catheter main body 10 has, in an end portion thereof (hereinafter, referred to as the front end portion) located in a front portion thereof (a right-hand portion in FIG. 1), a projection hole 20 that is punctured through a tubular wall of the catheter main body 10 and opens in a lateral direction (a downward direction in FIG. 1) perpendicular to the axial direction of the catheter main body 10.

Figure 4:
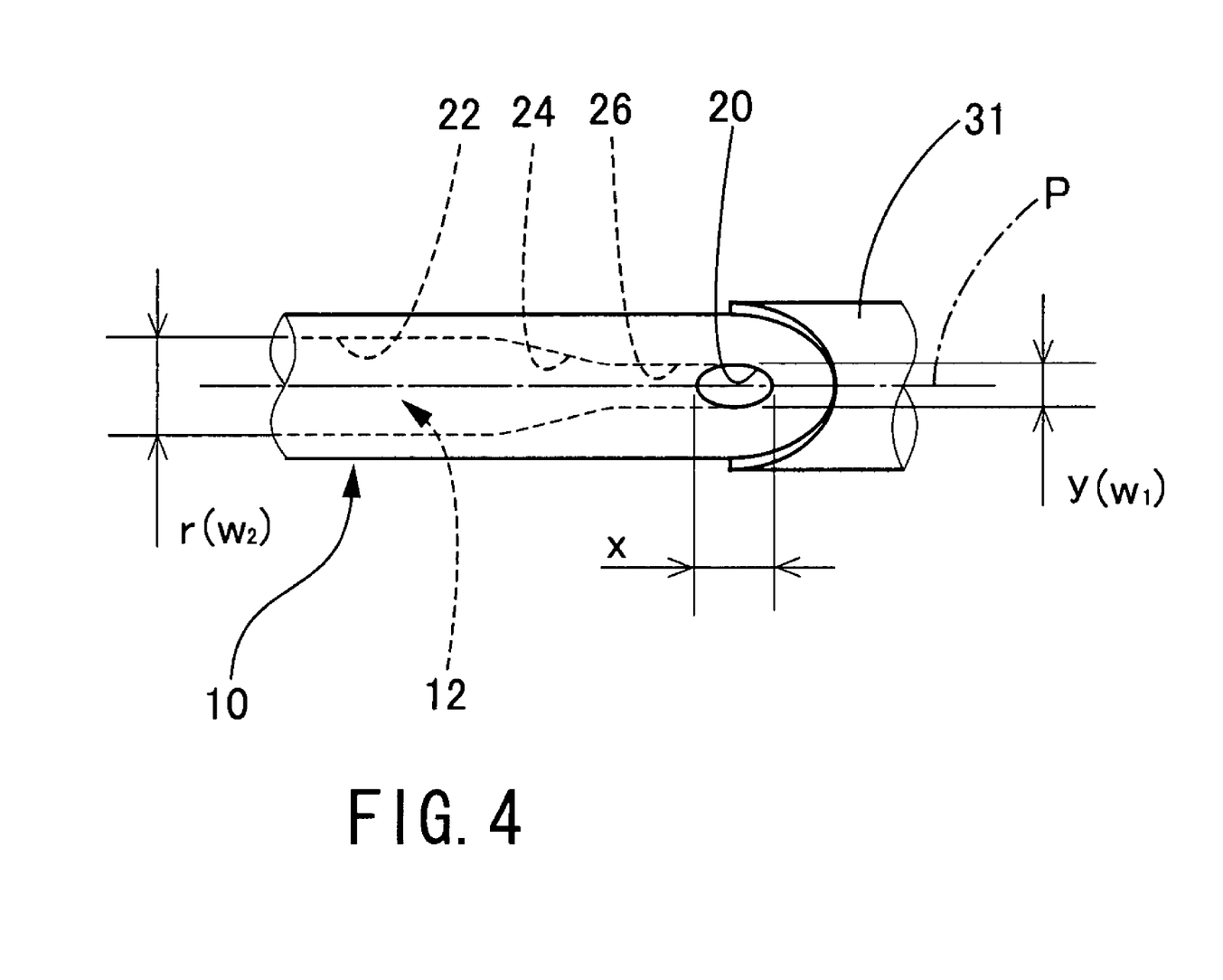
FIG. 4 is an explanatory view taken along arrow IV in FIG. 3.

As is apparent from FIG. 4, the projection hole 20 has an elliptic shape that is elongate in the axial direction of the catheter main body 10 and has a major axis x and a minor axis y each of which is shorter than an inner diameter r of an axially intermediate portion of the lumen 12. Thus, a width $w_1$ (corresponding to the minor axis y) of the projection hole 20 in a direction perpendicular to the axial direction of the catheter main body 10 and in a direction perpendicular to the direction in which the hole 20 opens, i.e., in a horizontal direction (a vertical direction in FIG. 4) is narrower, by an appropriate amount, than a width $w_2$ (corresponding to the inner diameter r) of the lumen 12 in the same direction. The width $w_1$ of the projection hole 20 is somewhat greater than an outer diameter of the needle portion 14 of the needle-like tubular member 16.

The lumen 12 formed in the catheter main body 10 has, in the front end portion of the catheter main body 10, an inner circumferential surface that formed into a narrowed shape corresponding to the shape of the projection hole 20, so that the lumen 12 communicates with the projection hole 20.

Thus, in the present embodiment, as shown in FIGS. 3 and 4, the inner circumferential surface of the lumen 12 of the catheter main body 10 has a generally tapered, cylindrical shape having different diameters between the front portion (a right-hand portion in FIGS. 3 and 4), and the rear portion (a left-hand portion in FIGS. 3 and 4), of the catheter main body 10, respectively. In other words, the lumen 12 includes a large-diameter portion 22, a tapered portion 24, and a small-diameter portion 26 that are arranged in the order of description in a direction from the rear portion, toward the front portion, of the catheter main body 10.

The large-diameter portion 22 that is located in the rear portion of the catheter main body 10 and communicates with the rear-end opening 18 has a cylindrical, inner circumferential surface that extends, in the axial direction, with the constant inner diameter. The small-diameter portion 26 that is located in the front portion of the catheter main body 10 and communicates with the projection hole 20 has a cylindrical, inner circumferential surface having an elliptic transverse cross section elongate in the direction in which the projection hole 20 is elongate. The tapered portion 24 that is located between the large-diameter portion 22 and the small-diameter portion 26 has an inner circumferential surface whose diameter gradually decreases in a direction toward the front end portion of the catheter main body 10, and connects between the large-diameter portion 22 and the small-diameter portion 26.

The lumen 12 communicates with the projection hole 20 such that in the vicinity of the projection hole 20, the width of the lumen 12 gradually decreases in the direction toward the projection hole 20. Thus, the lumen 12 opens, via the projection hole 20, in the lateral direction perpendicular to the axial direction of the catheter main body 10. As is apparent from this, the tapered portion 24 and the small-diameter portion 26 of the lumen 12 cooperate with each other to constitute a narrowed portion of the lumen 12.

The tapered portion 24 and the small-diameter portion 26 of the lumen 12 that are located in the front portion of the catheter main body 10 are curved downward toward the projection hole 20 opening downward. Thus, respective upper portions of the respective inner circumferential surfaces of the tapered portion 24 and the small-diameter portion 26 of the lumen 12 cooperate with each other to provide a guide surface 28 that is curved downward as it extends toward the front end portion of the catheter main body 10 and that has a generally convexly curved shape.

The tapered portion 24 that connects between the large-diameter portion 22 and the small-diameter portion 26 of the lumen 12 has a tapered, inner circumferential surface whose diameter gradually decreases in the direction toward the front end portion of the catheter main body 10, as described above. Thus, in the inner circumferential surface of the tapered portion 24, the portion other than the portion forming the guide surface 28 provides a leading surface 30 that is a part of the tapered surface whose diameter gradually decreases in a direction toward the small-diameter portion 26 having a narrowed width corresponding to the width of the projection hole 20.

Figure 5:
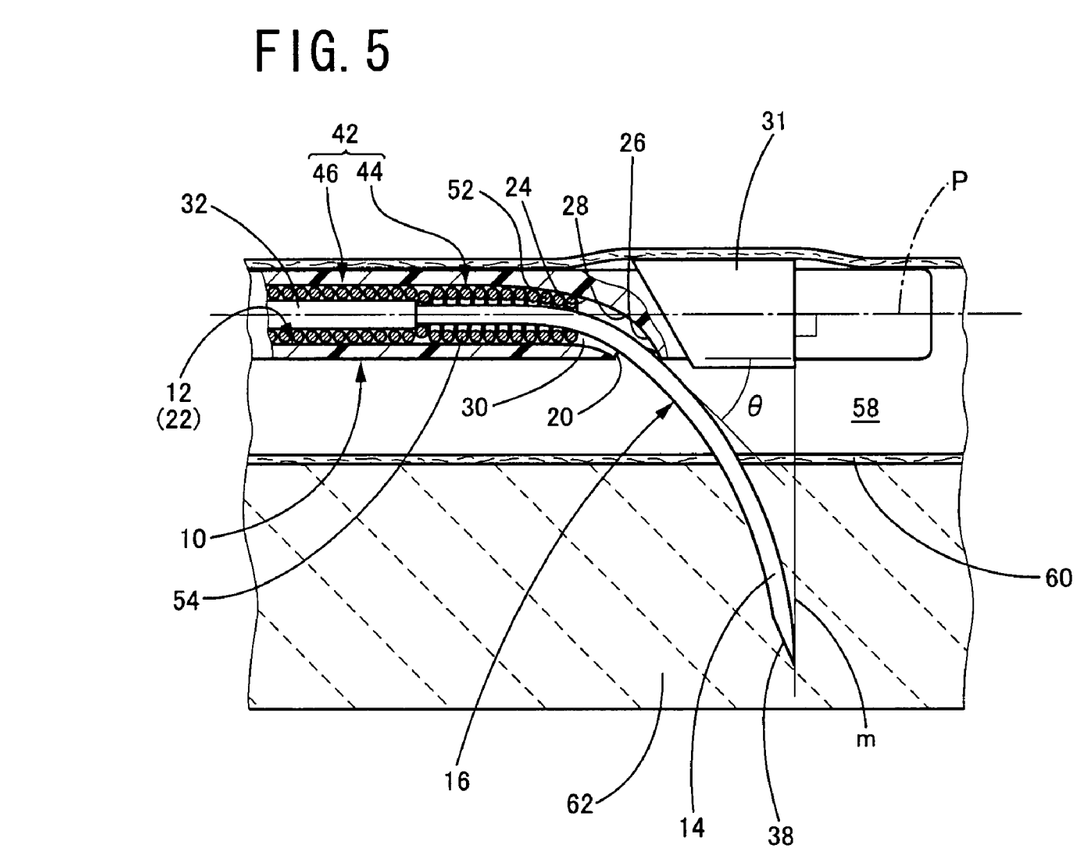
FIG. 5 is an explanatory view showing an example of a manner in which the medicinal-liquid injection catheter of FIG. 1 is used to inject an appropriate medicinal liquid to a lesion of cardiac muscle, more specifically described, showing a state in which a needle portion of the catheter is puncturing the cardiac muscle.

Thus, in the present embodiment as described hereafter, when the needle-like tubular member 16 is moved in the lumen 12 in the axial direction of the catheter main body 10 toward the front end portion of the same 10, the needle portion 14 of the needle-like tubular member 16 slides on the guide surface 28 and the leading surface 30 of the small-diameter portion 26 of the lumen 12, directly or via a protection member 42 externally fitted on the needle portion 14 so that the needle portion 14 is guided toward the projection hole 20 (see FIG. 5).

In FIGS. 1, 3, and 5, reference numeral 31 designates a marker tube as a marker member. The marker tube 31 is formed of a radiopaque material such as gold, platinum, a platinum-rhodium alloy, etc. The marker tube 31 has an inclined surface in one of axial open ends. Thus, a tubular wall of the marker tube 31 includes the longest portion and the shortest portion as seen in an axial direction thereof. The marker tube 31 is externally fitted on, and fixed to, the front end portion of the catheter main body 10, such that one of the longest and shortest portions of the tubular wall is aligned with the projection hole 20 formed in the front end portion of the catheter main body 10. The front end of the marker tube 31 substantially coincides with a tangential line m that is tangential to the needle-like tubular member 16 (the needle portion 14) in a state in which the needle-like tubular member 16 projects out of the projection hole 20 (see FIG. 5). Thus, in a state in which the catheter main body 10 is inserted in the blood vessel, a position of the projection hole 20 and a position of a tip of the needle-like tubular member 16 can be easily observed by radioscopy of the front end, and the longest and shortest portions of the tubular wall of the marker tube 31. In particular, in the present embodiment, the shortest portion of the tubular wall of the marker tube 31 is aligned with the projection hole 20, as shown in FIG. 3.

Meanwhile, as shown in FIGS. 1, 2, and 3, the needle-like tubular member 16 that is inserted in the lumen 12 is essentially constituted by a flexible thin tube. A portion of the needle-like tubular member 16 that is other than the needle portion 14 thereof as the free end portion thereof defines a medicinal-liquid flow duct portion 32 that is constituted by a thin tube having a length greater than the length of the catheter main body 10 and a diameter of approximately 0.4 mm. Thus, in this embodiment, the needle-like tubular member 16 is constituted by an integral body including the needle portion 14 and the medicinal-liquid flow duct portion 32.

The medicinal-liquid flow duct portion 32 of the needle-like tubular member 16 is formed of, e.g., a flexible synthetic resin material such as polytetrafluoroethylene or polyimide. The needle portion 14 is formed of, e.g., an elastic material such as a superelastic alloy, e.g., a Ni—Ti alloy, or a metal, e.g., stainless steel. A connector 34 is attached to one end of the medicinal-liquid flow duct portion 32 of the needle-like tubular member 16 in the opposite side to the needle portion 14. The flow duct portion 32 is connected, via the connector 34, to a syringe 36 as a medicinal-liquid supply device that supplies a desirable medicinal liquid.

Thus, the needle-like tubular member 16 is given a sufficiently high flexibility or elasticity, and accordingly it can be smoothly inserted in the lumen 12 of the catheter main body 10 that is inserted in the winding blood vessel, and can be moved in the axial direction of the catheter main body 10. Since the needle-like tubular member 16 is moved in the lumen 12 toward the front end portion of the catheter main body 10, eventually, the needle portion 14 is caused to project out of the projection hole 20 of the catheter main body 10 so that the needle portion 14 is caused to puncture the cardiac muscle. In addition, from the syringe 36, a medicinal liquid containing cells or a growth factor for regeneration of a necrotic portion of the cardiac muscle such as bFGF (basic fibroblast growth factor), VEGF (vascular endothelial cell growth factor), or HGF (hepatic cell growth factor), is introduced into the medicinal-liquid flow duct portion 32, and is injected outward from the opening of the tip of the needle portion 14.

As is apparent from FIG. 5, the needle portion 14 of the needle-like tubular member 16 has a convexly curved shape corresponding to that of the guide surface 28 provided in the tapered portion 24 and the small-diameter portion 26 of the lumen 12. Thus, in accordance with the movement of the needle-like tubular member 16 toward the front end portion of the catheter main body 10, the needle portion 14 is guided by the guide surface 28 formed in the tapered portion 24 and the small diameter portion 26 of the lumen 12 toward the projection hole 20 so as to project out of the projection hole 20. On this occasion, the respective curved shapes of the guide surface 28 and the needle portion 14 cooperate with each other to cause the needle portion 14 to project in the downward direction substantially perpendicular to the axial direction of the catheter main body 10.

The respective curved shapes of the guide surface 28 and the needle portion 14 may be decided, as needed, on ground of e.g., the rigidity of the needle portion 14. In addition, respective radii of curvature of respective curved portions of the guide surface 28 and the needle portion 14 are by no means limited to any specific values. However, in order that the respective curved shapes of the guide surface 28 and the needle portion 14 cooperate with each other to cause the needle portion 14 to project out of the projection hole 20, it is preferred that a projection angle θ of the needle portion 14 at a contact point between the needle portion 14 and the guide surface 28 is 45 degrees or larger.

Since the guide surface 28 and the needle portion 14 have the respective curved shapes corresponding to each other, it is assured that when a sufficient length of the needle portion 14 is caused to project out of the projection hole 20, as shown in FIG. 5, the tip of the needle portion 14 is located in the vicinity of the projection hole 20 so that the position of the needle portion 14 projecting out of the hole 20 is easily recognized. In addition, it is assured that the needle portion 14 is positioned in order that the tangential line m of the needle portion 14 perpendicularly intersects the central axis P of the catheter main body 10 near to the projection hole 20.

In the present embodiment, when the needle-like tubular member 16 is moved in the lumen 12 toward the front end portion of the catheter main body 10, as described above, the needle portion 14 is guided by the leading surface 30 provided in the tapered portion 24 of the lumen 12 to the projection hole 20 having the horizontal-direction width $w_1$ being somewhat greater than the outer diameter of the needle portion 14. Therefore, when the needle-like tubular member 16 is moved toward the front end portion of the catheter main body 10, eventually, the needle portion 14 is caused to project out of the projection hole 20 while it is prevented from being deflected in the horizontal direction.

FIG. 5 shows that an opening end surface 38 of the free open end of the needle portion 14, the tip surface of the needle portion 14, is so inclined as to extend downward as seen in the direction toward the front end portion of the catheter main body 10. However, conversely, the opening end surface 38 of the needle portion 14 may be so inclined as to extend upward as seen in the direction toward the front end portion of the catheter main body 10. An outer surface of the needle portion 14 is plated with gold, platinum, platinum-rhodium alloy, etc. Thus, when the needle-like tubular member 16 is moved in the lumen 12, or when the needle portion 14 is caused to puncture and advance into the cardiac muscle, the position of the needle portion 14 can be easily recognized by radioscopy.

Meanwhile, as shown in FIGS. 1 through 3, an intermediate tube 40 is externally fitted on the needle-like tubular member 16 except the front end portion thereof in which the needle portion 14 is provided. The intermediate tube 40 has an outer diameter that assures that the tube 40 can be inserted in the lumen 12 of the catheter main body 10, and is formed of a metal such as stainless steel or a synthetic resin having an elasticity or a flexibility. In the state in which the intermediate tube 40 is externally fitted on the needle-like tubular member 16, the intermediate tube 40 is integrally bonded with, e.g., an adhesive to the end portion of the needle-like tubular member 16 that is opposite to the needle portion 14.

In the side of a front end of the intermediate tube 40, a protection member 42 is externally fitted on the needle-like tubular member 16 so as to protect an outer circumferential surface of the needle portion 14.

The protection member 42 is constituted by a coil including a coil-spring portion 44 and a strand portion 46. The coil-spring portion 44 is obtained by winding a single metallic wire such as a stainless-steel wire, and the strand portion 46 is obtained by stranding a plurality of metallic wires such as stainless-steel wires. The coil-spring portion 44 includes a first spring portion 54 and a second spring portion 52. The first spring portion 54 has a widened pitch as to be compressible and expansible and produces a biasing force against a compressive or expansive load. The second spring portion 52 includes coil's turns in which each pair of adjacent coil's turns contact each other, and exhibits a flexibility in a direction intersecting an axial direction thereof. The first spring portion 54 of the coil-spring portion 44 and the strand portion 46 are integrally bonded by, e.g., brazing each other.

Thus, the protection member 42 is given as an integral body including the coil-spring portion 44 and the strand portion 46, such that the protection member 42 has an overall length that can cover the entirety of the needle portion 14 of the needle-like tubular member 16 and the front end portion of the medicinal-liquid flow duct portion 32 in the side of the needle portion 14. The protection member 42 has an outer diameter that can be inserted in the lumen 12 of the catheter main body 10 and an inner diameter that is greater by an appropriate value than the outer diameter of the needle portion 14.

In the protection member 42, the second spring portion 52 of the coil-spring portion 44 provides a flexible portion that externally surrounds the free end portion of the needle portion 14 of the needle-like tubular member 16, so as to cover the tip thereof. The first spring portion 54 of the coil-spring portion 44 provides a compressible and expansible portion that externally surrounds the portion of the needle-like tubular member 16 other than the free end portion of the needle portion 14. Meanwhile, the strand portion 46 of the protection member 42 provides a support portion that is externally fitted on the front end portion of the medicinal-liquid flow duct portion 32 of the needle-like tubular member 16 in the side of the needle portion 14.

The protection member 42 is integrally bonded, at the opposite end portion of the strand portion 46 that is opposite to the first spring portion 54, to the intermediate tube 40 with, e.g., an adhesive. In addition, the protection member 42 is integrally bonded, at the bonded portions between the strand portion 46 and the first spring portion 54, to the rear end portion of the needle portion 14 by, e.g., brazing.

An outer surface of the second spring portion 52 of the protection member 42 is plated with a radiopaque material such as gold, platinum, or platinum-rhodium alloy. A direction of winding of the metallic wire used to form the strand portion 46 is opposite to a direction of winding of the metallic wire used to form the coil-spring portion 44 including the first and second spring portions 54 and 52.

In the state in which the protection member 42 and the intermediate tube 40 are externally fitted on, and fixed to, the needle-like tubular member 16, the protection member 42 and the intermediate tube 40 are inserted, together with the needle-like tubular member 16, in the lumen 12 of the catheter main body 10, such that the elements 42, 40, and 16 are movable as a unit in the axial direction of the catheter main body 10. Since the intermediate tube 40 is externally fitted on the needle-like tubular member 16 and the direction of winding of the metallic wire used to form the coil-spring portion 44 and the direction of winding of the metallic wire used to form the strand portion 46 are opposite to each other, a pushability of the needle-like tubular member 16 is enhanced in the state that the needle-like tubular member 16 is moved in the lumen 12. In addition, since the outer surface of the second spring portion 52 of the protection member 42 that covers the tip of the needle portion 14 of the needle-like tubular member 16 is plated with the radiopaque material, a position of the tip of the needle portion 14 can be easily recognized by radioscopy of the second spring portion 52 when the needle-like tubular member 16 is moved in the lumen 12.

In particular, since the needle-like tubular member 16 is moved in the lumen 12 in the state in which the tip of the needle portion 14 is surrounded by the second spring portion 52, the second spring portion 52 is always located between the tip of the needle portion 14 and the inner circumferential surface of the lumen 12. Thus, when the needle-like tubular member 16 is moved in the lumen 12, the tip of the needle portion 14 can be effectively prevented from being contacted with, or being lodged by, the inner surface of the lumen 12.

As described above, the lumen 12 includes the tapered portion 24 and the small-diameter portion 26, and communicates with the projection hole 20 such that the width of the lumen 12 gradually decreases in the vicinity of the hole 20. Therefore, as shown in FIG. 5, when the needle-like tubular member 16 is moved in the lumen 12 to the front end portion of the catheter main body 10 so that the needle portion 14 of the needle-like tubular member 16 reaches the tapered portion 24 of the lumen 12, the second spring portion 52 of the protection member 42 is engaged with the inner surface of the tapered portion 24 to be inhibited from being further moved.

In the above-indicated state, if the needle-like tubular member 16 is further moved, the needle-like tubular member 16 is moved relative to the second spring portion 52 so that the tip of the needle portion 14 is exposed out of the second spring portion 52. In this state, the first spring portion 54 of the protection member 42 is compressed by a relative movement amount of the second spring portion 52, namely a movement amount of the needle-like tubular member 16. Thus, when the second spring portion 52 is engaged with the tapered portion 24, the smooth movement of the needle-like tubular member 16 is not disturbed. Eventually, the protection member 42 is inhibited from projecting out of the projection hole 20 and only the needle portion 14 is allowed to project out of the hole 20. As is apparent from this in the present embodiment, the tapered portion 24 of the lumen 12 provides an engaging portion.

Next, there will be described a method in which the medicinal-liquid injection catheter of the present embodiment constructed as described above is used to inject an appropriate medicinal liquid to a lesion such as a substantially necrotic portion of the cardiac muscle.

When a medicinal-liquid injection treatment in which the medicinal-liquid injection catheter is used is carried out, first, the needle-like tubular member 16 with the intermediate tube 40 and the protection member 42 externally fitted thereon and fixed thereto, is inserted over an appropriate length thereof into the lumen 12 of the catheter main body 10. Thus, the medicinal-liquid injection catheter is prepared.

Subsequently, the catheter main body 10 is inserted in a blood vessel (an artery) located on a surface of the cardiac muscle. This operation is carried out by radioscopy while the position of the marker tube 31 externally fitted on, and fixed to, the front end portion of the catheter main body 10 is observed on, e.g., a monitor. More specifically described, when the catheter main body 10 is inserted in the blood vessel, if the marker tube 31 reaches a predetermined target position in the blood vessel, the operation of inserting the catheter main body 10 is suspended. On this occasion, the shortest and longest portions of the marker tube 31 are recognized. Thereafter, the position of the catheter main body 10 in an axial direction of the blood vessel is finely adjusted, while the catheter main body 10 is rotated about its axis line so that the projection hole 20 is so positioned as to open toward an appropriate portion of the lesion of the cardiac muscle to which the medicinal liquid is to be injected.

Before this inserting operation in which the catheter main body 10 is inserted in the blood vessel, a known guide wire may be inserted in the blood vessel so that the catheter main body 10 may be inserted in the blood vessel along the guide wire. To carry out this operation, the medicinal-liquid catheter needs to be structured such that the catheter main body 10 has, in addition to the inner lumen 12 in which the needle-like tubular member 16 is inserted, another inner lumen in which the guide wire is so inserted as to be movable in an axial direction thereof.

In addition, the catheter main body 10 may have, on an outer circumferential surface thereof, an expansible and compressible balloon having a known structure. In this case, when the catheter main body 10 reaches the predetermined target position in the blood vessel, the balloon may be expanded so that the catheter main body 10 can be fixedly held in the blood vessel. To this end, the catheter main body 10 needs to have another lumen for the balloon in which a fluid is caused to flow so as to expand the balloon.

Meanwhile, if it is recognized by radioscopy that the catheter main body 10 is positioned at the desired position in the blood vessel, the needle-like tubular member 16, inserted in the lumen 12 of the catheter main body 10, is moved toward the front end portion of the catheter main body 10. The operation of moving the needle-like tubular member 16 in the lumen 12 and the operation of projecting the needle portion 14 out of the projection hole 20 are carried out by hand motion, a known screw mechanism or the like.

As described above, in the medicinal-liquid injection catheter of the present embodiment, the tip of the needle portion 14 of the needle-like tubular member 16 is surrounded by the second spring portion 52 of the protection member 42, and accordingly the tip of the needle portion 14 is prevented from being contacted with, or being caught by, the inner circumferential surface of the lumen 12. Thus, the needle-like tubular member 16 can be smoothly moved in the lumen 12. In addition, the inner circumferential surface of the lumen 12 can be prevented from being scarred by the tip of the needle portion 14.

In addition, the intermediate tube 40 is externally fitted on almost all of the medicinal-liquid flow duct portion 32 of the needle-like tubular member 16, and the respective directions of winding of the strand portion 46 and the coil-spring portion 44 of the protection member 42, externally fitted on the front end portion of the needle-like tubular member 16 located on the side of the needle portion 14, are opposite to each other. Thus, the needle-like tubular member 16 enjoys an improved pushability. Therefore, the needle-like tubular member 16 can be smoothly moved in the lumen 12. In addition, the respective surfaces of the needle portion 14 and the second spring portion 52 of the protection member 42 are plated with the radiopaque material. Thus, when the needle-like tubular member 16 is moved in the lumen 12, the position of the needle portion 14 can be easily recognized by radioscopy. Therefore, the operation to move the needle-like tubular member 16 in the lumen 12 can be smoothly and accurately carried out.

After the movement of the needle-like tubular member 16 in the lumen 12 leads the tip of the needle portion 14 of the needle-like tubular member 16 to the tapered portion 24 of the lumen 12, the needle-like tubular member 16 is further moved in the lumen 12. As a result, as shown in FIG. 5, the needle portion 14 is caused to project out of the projection hole 20, so as to penetrate a vessel wall 60 of a blood vessel 58 and puncture a lesion of a cardiac muscle 62.

As described above, in the medicinal-liquid injection catheter of the present embodiment, when the tip of the needle portion 14 reaches the tapered portion 24 of the lumen 12, the second spring portion 52 of the protection member 42 is caused to engage the inner circumferential surface of the tapered portion 24. Therefore, when the needle-like tubular member 16 is further moved, the first spring portion 54 of the protection member 42 is compressed, so that only the needle portion 14 of the needle-like tubular member 16 is caused to project out of the projection hole 20. Since the needle portion 14 is slid on, and guided by, the guide surface 28 and the leading surface 30 of the tapered and small-diameter portions 24 and 26 of the lumen 12 via the second spring portion 52 of the protection member 42, the needle portion 14 is caused to project out of the projection hole 20, at a location near thereto, in a downward direction perpendicular to a central axis P of the catheter main body 10. When the needle portion 14 is drawn into the lumen 12 and the needle-like tubular member 16 is moved backward in the lumen 12, the second spring portion 52 of the protection member 42 is disengaged from the tapered portion 24 of the lumen 12 and the first spring portion 54 is returned to its initial state before compression.

When the needle portion 14 reaches an appropriate depth of the lesion of the cardiac muscle 62, the movement of the needle-like tubular member 16 is ended. Then, from the syringe 36 connected to the end of the needle-like tubular member 16 in the opposite side to the needle portion 14, a medicinal liquid containing cells or a growth factor to regenerate the cardiac muscle 62 is introduced into an inner hole of the needle-like tubular member 16. Eventually, the medicinal liquid is ejected outward through the opening of the tip of the needle portion 14, and is injected into the lesion of the cardiac muscle 62.

After the medicinal liquid is injected to the portion of the lesion of the cardiac muscle 62, the needle-like tubular member 16 is moved backward in the catheter main body 10, and the needle portion 14 is drawn into the catheter main body 10. Subsequently, the operation of injecting the medicinal liquid to the lesion of the cardiac muscle 62 is repeated a plurality of times at a plurality of positions. Thus, the medicinal liquid is injected to a plurality of portions of the lesion of the cardiac muscle 62.

Thus, in the medicinal-liquid injection catheter of the present embodiment, the tip of the needle portion 14 is surrounded and protected by the second spring portion 52 of the protection member 42. Therefore, the needle-like tubular member 16 can be smoothly moved in the lumen 12 without damage of the inner circumferential surface of the lumen 12 because the tip of the needle portion 14 does not contact or lodge the inner circumferential surface of the lumen 12.

Thus, with the medicinal-liquid injection catheter of the present embodiment, the operation of injecting the medicinal liquid to the lesion of the cardiac muscle 62 can be smoothly carried out. In addition, a good operating condition of the medicinal-liquid injection catheter can be stably assured.

Moreover, in the medicinal-liquid injection catheter, the protection member 42 including the second spring portion 52 that surrounds the tip of the needle portion 14 has such a simple structure that a metallic wire or wires is or are wound or stranded. Thus, the above-indicated excellent advantages can be realized with the very simple structure.

In addition, in the medicinal-liquid injection catheter of the present embodiment, when the protection member 42, externally fitted on and fixed to the front end portion of the needle-like tubular member 16 in the side of the needle portion 14, is moved in the lumen 12, together with the needle-like tubular member 16, up to the tapered portion 24 of the lumen 12, the second spring portion 52 of the protection member 42 is engaged with the inner circumferential surface of the tapered portion 24 of the lumen 12, so that the first spring portion 54 is compressed and only the needle portion 14 is caused to project out of the projection hole 20. Thus, the needle portion 14 of the needle-like tubular member 16 can be easily and reliably caused to puncture the lesion of the cardiac muscle 62 without being interfered with by the protection member 42.

Moreover, in the present medicinal-liquid injection catheter, the marker tube 31 formed of the radiopaque material is externally fitted on, and fixed to, the front end portion of the catheter main body 10, and the respective surfaces of the needle portion 14 of the needle-like tubular member 16 and the second spring portion 52 of the protection member 42 are plated with the radiopaque material. Thus, on the occasion when the catheter main body 10 is inserted in the blood vessel 58, when the needle-like tubular member 16 is moved in the lumen 12 of the catheter main body 10 inserted in the blood vessel 58, or when the needle portion 14 is caused to puncture the cardiac muscle 62, the position of the catheter main body 10, or the position of the needle portion 14 can be easily recognized by radioscopy. Therefore, the operation of injecting the medicinal liquid to the lesion of the cardiac muscle 62 can be carried out more smoothly.

Moreover, in the medicinal-liquid injection catheter in the present embodiment, the needle portion 14 is slid on, and guided by, the guide surface 28 and the leading surface 30 of the lumen 12 directly or via the second spring portion 52 of the protection member 42 externally fitted on the needle portion 14 so that the needle portion 14 is directed toward the projection hole 20. Thus, through the projection hole 20, the needle portion 14 is caused to project such that the needle portion 14 extends at a position near the hole 20, in the downward direction perpendicular to the central axis P of the catheter main body 10. Thus, the needle-like tubular member 16 has a great component force in the direction of advancing in the lesion of the cardiac muscle 62. Consequently the needle portion 14 can be smoothly advanced in the cardiac muscle 62.

In addition, in the medicinal-liquid injection catheter of the present embodiment, the horizontal-direction width $w_1$ of the projection hole 20 is somewhat greater than the outer diameter of the needle portion 14. Moreover the needle portion 14 is guided toward the projection hole 20 by the leading surface 30 in the form of the tapered surface whose diameter gradually decreases, in the tapered portion 24 of the lumen 12, toward the hole 20. Thus, the needle portion 14 is caused to project through the projection hole 20, while being prevented from being moved in the horizontal directions.

Therefore, in the medicinal-liquid injection catheter of the present embodiment, the needle portion 14 can be stably caused to project through the projection hole 20 in the certain direction without being deflected in the horizontal directions. Consequently the needle portion 14 can be reliably caused to be advanced in the appropriate portion of the lesion of the cardiac muscle 62. Thus, the operation of injecting the medicinal liquid to the lesion of the cardiac muscle 62 can be carried out more smoothly. In addition, the good operating capability of the medicinal-liquid injection catheter can be more effectively assured.

Figure 6:
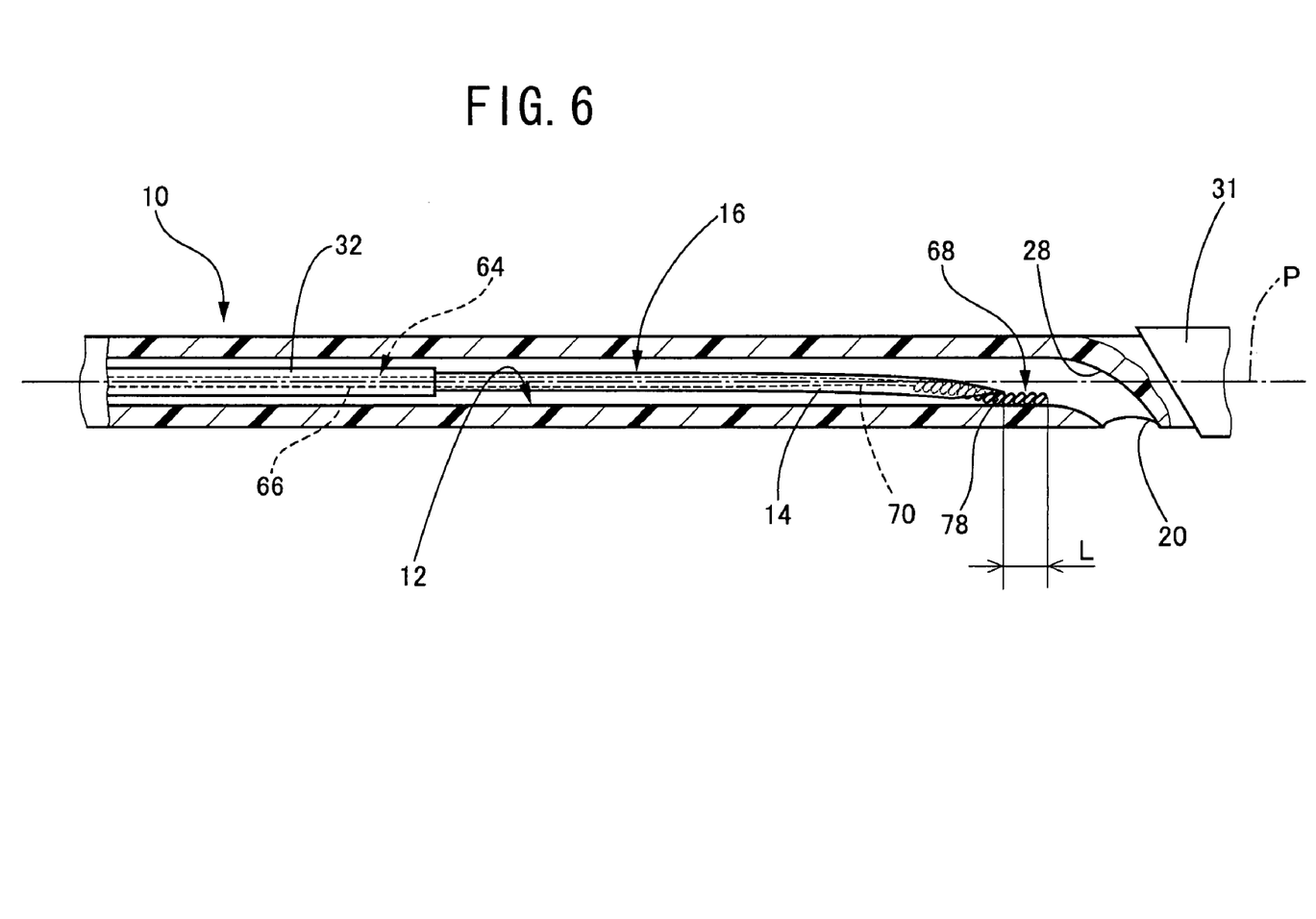
FIG. 6 is a view corresponding to FIG. 3, showing another medicinal-liquid injection catheter having a structure in accordance with the present invention.
Figure 7:
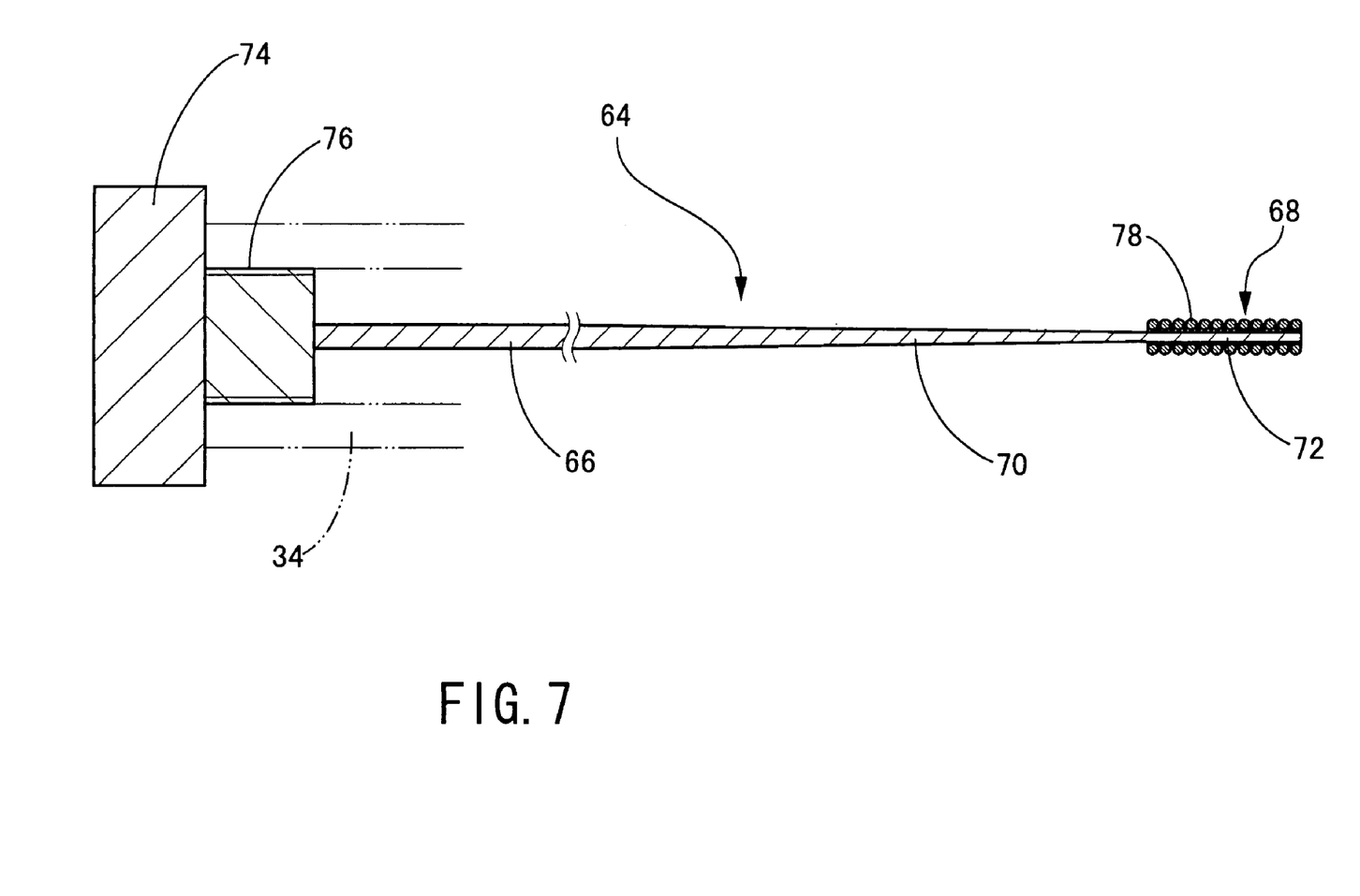
FIG. 7 is an enlarged, longitudinal cross-sectional explanatory view of a protection member employed by the medicinal-liquid injection catheter of FIG. 6.

FIGS. 6 and 7 show another embodiment that differs from the above-described embodiment in the structure of a protection member. The same reference numerals as those in FIGS. 1 through 5 are used in FIGS. 6 and 7 if they designate the same elements or parts of the former embodiment so the description of those elements or parts is omitted.

In the medicinal-liquid injection catheter of the present embodiment, a protection member 64 is inserted in an inner hole of a needle-like tubular member 16 provided in a lumen 12 of a catheter main body 10, such that a free end portion of the protection member 64 projects out of an opening of a tip of a needle portion 14. The protection member 64 includes an insertion portion 66 that is an axial portion inserted in the needle-like tubular member 16 and a flexible portion 68 as the free end portion thereof projecting out of the opening of the tip of the needle portion 14. In other words, in the present embodiment, the protection member 64 is constituted by an integral component including the insertion portion 66 and the flexible portion 68.

The insertion portion 66 as part of the protection member 64 is constituted by a single metallic wire such as a stainless-steel wire that is longer than the needle-like tubular member 16. The insertion portion 66 has, in one lengthwise end portion thereof, a tapered portion 70 whose diameter gradually decreases toward a front end thereof, and a small-diameter portion 72 that integrally extends from one end of the tapered portion 70. Thus, the insertion portion 66 as a whole exhibits a flexibility or an elasticity, and in particular the small-diameter portion 72 located on the side of the end of the portion 66 exhibits a higher flexibility. Consequently the protection member 64 can be smoothly moved forward and backward in the inner hole of the winding or curving needle-like tubular member 16. In addition, as described above, the flexible portion 68 projecting out of the opening of the tip of the curved needle portion 14 is caused to contact closely an inner circumferential surface of a free end portion of the needle portion 14.

The insertion portion 66 of the protection member 64 has, in the other lengthwise end portion thereof, a stopper 74 as an integral portion thereof. The stopper 74 includes a threaded portion 76 that is threadedly engaged with the above-described connector 34 located on the side of a rear end portion of the catheter main body 10, in a state in which the protection member 64 is inserted in the needle-like tubular member 16. In the state in which the threaded portion 76 is threadedly engaged with the connector 34, the protection member 64 is detachably attached to the connector 34. Consequently the protection member 64 is prevented from being moved forward, in the inner hole of the needle-like tubular member 16 toward the side of the needle portion 14. Thus, the protection member 64 and the needle-like tubular member 16 are moved together with each other in the lumen 12 of the catheter main body 10. In the state in which the stopper 74 is attached to the connector 34, the flexible portion 68 projects, by an appropriate amount L, out of the opening of the tip of the needle portion 14. The amount L ranges, e.g., from 1 mm to 3 mm.

The flexible portion 68 is constituted by a coil 78 that is externally fitted on, and fixed to, the small-diameter portion 72 of the flexible portion 68. More specifically described, the coil 78 constituting the flexible portion 68 is obtained by winding a metallic wire formed of a radiopaque material such as gold, platinum, or platinum-rhodium alloy, and has a flexibility. The coil 78 has an inner diameter that assures that the coil 78 can be externally fitted on the small-diameter portion 72 of the insertion portion 66, and an outer diameter that is smaller than the opening of the tip of the needle portion 14 of the needle-like tubular member 16. In the state in which the flexible coil 78 is externally fitted on the highly flexible small-diameter portion 72 of the insertion portion 66, both end portions of the coil 78 are integrally bonded by, e.g., brazing to the small-diameter portion 72. Thus, the one end portion of the protection member 64, opposite to the stopper 74 of the insertion portion 66, provides the flexible portion 68 exhibiting a soft spring characteristic in a direction perpendicular to an axial direction of the protection member 64.

In the case where the medicinal-liquid injection catheter of the present embodiment is used to inject an appropriate medicinal liquid to a lesion of a cardiac muscle (62), such as a substantially necrotic portion, first, the needle-like tubular member 16 is inserted by an appropriate amount in the lumen 12 of the catheter main body 10. After, or before, this operation, the protection member 64 is inserted in the inner hole of the needle-like tubular member 16, such that the flexible portion 68 projects, by the regulated amount L, out of the opening of the tip of the needle portion 14, and the stopper 74 of the insertion portion 66 is fastened to the connector 34.

Subsequently, the catheter main body 10 is inserted in a blood vessel (58) of the cardiac muscle (62), up to an appropriate position. Then, in the state in which the protection member 64 is inserted in the inner hole of the needle-like tubular member 16, the needle-like tubular member 16 is moved in the lumen 12 of the catheter main body 10.

After the tip of the needle portion 14 of the needle-like tubular member 16 reaches, in the lumen 12, the position where the projection hole 20 is formed, the movement of the needle-like tubular member 16 is suspended, and the stopper 74 is disengaged from the connector 34. Thus, the protection member 64 is moved backward in the needle-like tubular member 16 to a position where the flexible portion 68 is retracted in the needle portion 14.

Subsequently, the needle-like tubular member 16 is moved again in the lumen 12 toward the front end portion of the catheter main body 10 so that the needle portion 14 projects out of the projection hole 20. Thus, the needle portion 14 punctures the lesion of the cardiac muscle (62) and advances in the lesion by an appropriate amount.

Then, the protection member 64 is removed from the lumen 12. Thereafter, a syringe (36) is attached to the connector 34. Then, the medicinal liquid is injected from the syringe (36) to the lesion of the cardiac muscle (62) through the needle portion 14.

This series of operations, except the operation of manipulating the protection member 64 and the operation of attaching the syringe (36) to the connector 34 in place of the protection member 64, are the same as those carried out using the medicinal-liquid injection catheter of the preceding embodiment.

In the present embodiment, the protection member 64 is inserted in the needle-like tubular member 16 and, in the state in which the flexible portion 68 that exhibits the soft spring characteristic in the direction perpendicular to the axial direction is closely contacted with the inner circumferential surface of the free end portion of the needle portion 14 and is projected by the regulated amount L out of the opening of the tip of the needle portion 14, the needle-like tubular member 16 and the protection member 64 are moved together with each other in the lumen 12 of the catheter main body 10. Therefore, when the needle-like tubular member 16 is moved in the lumen 12 in the axial direction, the flexible portion 68 of the protection member 64 is always located between the tip of the needle portion 14 and the inner circumferential surface of the lumen 12 so as to effectively prevent the tip of the needle portion 14 from being contacted with, or being lodged in, the inner surface of the lumen 12. In addition, since the rigidity of the needle-like tubular member 16 is effectively increased by the protection member 64, the needle-like tubular member 16 can be easily inserted in the catheter main body 10 along the central axis P thereof. Consequently the needle-like tubular member 16 can be easily inserted and can be prevented from scarring the inner surface of the lumen 12.

Therefore, in the medicinal-liquid injection catheter of the present embodiment, the needle-like tubular member 16 can be moved smoothly in the lumen 12 without scarring the inner surface of the lumen 12. Thus, the operation of injecting the medicinal liquid to the lesion of the cardiac muscle (62) can be smoothly carried out. In addition, a good operating condition of the medicinal-liquid injection catheter can be stably assured.

Moreover, in the present medicinal-liquid injection catheter, the protection member 64 has the considerably simple structure in which the insertion portion 66 constituted by the single metallic wire and the flexible portion 68 including the free end portion on and to which the coil 78 is externally fitted and fixed, are formed to be integral with each other. Thus, the above-indicated excellent advantages can be easily realized with the simple structure.

In addition, in the present medicinal-liquid injection catheter, the protection member 64 including the insertion portion 66 constituted by the long metallic wire is inserted, over its entire length thereof, in the inner hole of the needle-like tubular member 16. Therefore, the rigidity of the needle-like tubular member 16 is increased by an appropriate amount. Consequently a pushability of the needle-like tubular member 16 when inserted into the lumen 12 can be advantageously increased. Thus, the needle-like tubular member 16 can be smoothly moved in the lumen 12. In addition, the needle portion 14 can be smoothly and reliably advanced in the cardiac muscle (62).

Moreover, in the medicinal-liquid injection catheter of the present embodiment, the flexible portion 68 is formed of the radiopaque material. Thus, when the needle-like tubular member 16 is moved in the lumen 12 of the catheter main body 10, the position of the needle portion 14 can be easily recognized by radioscopy. Therefore, the operation of injecting the medicinal liquid to the lesion of the cardiac muscle (62) can be carried out smoothly.

While the concrete structures of the present invention has been described, the above-described structures are only examples and that the present invention is by no means limited by the above explanations.

For example, the protection member 42 and 64 may be formed of a material different from the metallic material, and may be given a shape different from that of the coil.

More specifically described, in the case where the protection member 42 includes the first and second spring portions 54 and 52 and the strand portion 46, the second spring portion 52 as the flexible portion may be constituted by a tubular member formed of such as a rubber or a synthetic resin that has a high flexibility. In addition, the first spring portion 54 as the expansible and compressible portion may be formed of a rubber or a synthetic resin that has an elasticity and may be constituted by a simple tubular member, a tubular member having slits, or a tubular member having bellows.

In the case where the protection member 42 including the first and second spring portions 54 and 52 and the strand portion 46 is constituted by a coil, the coil may be constituted by a wire formed of a non-metallic material.

In the case where the protection member 64 includes the insertion portion 66 and the flexible portion 68, the insertion portion 66 may be constituted by a wire formed of a rubber or a synthetic resin that has a flexibility. In addition, the flexible portion 68 may be constituted by a wire formed of a rubber or a synthetic resin that has a high flexibility. In the flexible portion 68, the insertion portion 66 may be constituted by a wire having a diameter smaller than that of the insertion portion 66 and thereby having a flexibility higher than that of the same 66.

The structure employed to support the protection member 42 and 64 on the needle-like tubular member 16 so as to be movable together with the same 16, is not limited to those shown in the above-described two embodiments.

It is possible that the guide surface 28 having the convexly curved shape may be formed in the respective inner circumferential surfaces of the tapered portion 24 and the small-diameter portion 26 of the lumen 12, while the needle portion 14 has a straight shape.

It goes without saying that the structure employed to cause the protection member 42 to engage the inner circumferential surface of the lumen 12 and thereby prevent the protection member 42 from projecting out of the projection hole 20 is not limited to that shown in the above-described embodiment.

The medicinal-liquid injection catheter may employ not only the protection member 42 that is externally fitted on and fixed to the needle-like tubular member 16 so as to protect the tip of the needle portion 14 thereof, but also the protection member 64 inserted in the needle-like tubular member 16 so as to protect the tip of the needle portion 14 thereof.

The shape and number of the leading surface 30 formed in the inner circumferential surface of the lumen 12 are not limited to those shown in the above-described embodiments.

The above-described embodiments show concrete embodiments in which the present invention is applied to the medicinal-liquid injection catheter that injects the medicinal liquid to the lesion of the cardiac muscle. However, the present invention can be advantageously applied to a medicinal-liquid injection catheter for injecting a medicinal liquid to a tissue of a living being other than the cardiac muscle, or a medicinal-liquid injection apparatus that does not belong to the category of catheters for injecting a medicinal liquid to a lesion of a cardiac muscle or a tissue of a living being other than the cardiac muscle.

The present invention may be embodied with various changes, modifications, and improvements that may occur to a person skilled in the art, though those changes, modifications, and improvements are not described any more. It is to be understood that those embodiments fall within the scope of the present invention, without departing from the spirit of the same.

What is claimed is:

1. A medicinal-liquid injection apparatus, comprising:
   a tubular main body which is insertable in a body of a living being and which has an inner lumen and a projection hole through which the lumen opens outward;
   a tubular member which includes a needle portion as a free end portion thereof, which is supplied with a medicinal liquid, and which is insertable in the lumen of the tubular main body such that the tubular member is movable in an axial direction of the tubular main body and the needle portion is caused to project outward through the projection hole of the tubular main body; and
   a protection member, which includes an insertion portion, which is detachably inserted in an inner hole of the tubular member, and a flexible portion, which is arranged in an end of the insertion portion and which projects out of an opening of a tip of the needle portion of the tubular member in a state in which the insertion portion is inserted in the inner hole of the tubular member so that the flexible portion is interposed between the inner circumferential surface of the lumen and the tip of the needle portion of the tubular member,
   wherein when the flexible portion exits the tubular member and contacts the inner circumferential surface of the lumen, the flexible portion urges the tip of the needle portion away from contact with the inner circumferential surface of the lumen, and when the needle portion of the tubular member is caused to project out of the projection hole of the tubular main body so as to puncture a tissue of the body of the living being in a state in which the tubular main body is inserted and located in the body of the living being, the medicinal liquid supplied through the tubular member is injected to the tissue of the body in a state in which the protection member is removed from the tubular member.

2. The medicinal-liquid injection apparatus according to claim 1, wherein the flexible portion of the protection member is at least partly formed of a radiopaque material.

3. The medicinal-liquid injection apparatus according to claim 1, further comprising a marker member formed of a radiopaque material which is provided in a vicinity of the projection hole of the tubular main body.

4. The medicinal-liquid injection apparatus according to claim 1, wherein a portion of the lumen in a vicinity of the projection hole is constituted by a narrowed portion which is narrower than a diameter of the lumen.

5. The medicinal-liquid injection apparatus according to claim 1, wherein the tubular member is connected to a medicinal-liquid supply device which supplies the medicinal liquid to the tubular member.

6. The medicinal-liquid injection apparatus according to claim 1, wherein the insertion portion of the protection member is constituted by a long wire.

7. The medicinal-liquid injection apparatus according to claim 1, wherein the flexible portion of the protection member is constituted by a coil spring which is fixed to the insertion portion.

8. The medicinal-liquid injection apparatus according to claim 1, wherein the projection hole is formed in the tubular main body, such that the projection hole opens in a direction perpendicular to the axial direction of the tubular main body, and the inner circumferential surface of the lumen includes a guide surface which guides the needle portion toward the projection hole, when the tubular member is moved in the axial direction and the needle portion slides on the guide surface, and which is formed to have a convexly curved shape which is curved toward the direction in which the projection hole opens.

9. The medicinal-liquid injection apparatus according to claim 8, wherein the needle portion of the tubular member has a curved shape corresponding to the guide surface formed in the tubular main body and having the convexly curved shape, and wherein the convexly curved shape of the guide surface and the curved shape of the needle portion cooperate with each other to cause the needle portion to project out of the projection hole, toward a direction approximating the direction perpendicular to the axial direction of the tubular main body.

10. A medicinal-liquid injection apparatus, comprising:
    a tubular main body which is constituted by a tubular body insertable in a body of a living being and which has an inner lumen and a non-circular projection hole opening the lumen outward, said projection hole has a width in a direction perpendicular to an axial direction of the tubular main body smaller than a width in the axial direction of the tubular main body;
    a tubular member which includes a needle portion, which is supplied with a medicinal liquid, and which is insertable in the lumen of the tubular main body such that the tubular member is movable in the axial direction and the needle portion is caused to project outward through the projection hole; and
    a leading surface which is provided in an inner circumferential surface of the lumen of the tubular main body, and which guides the needle portion of the tubular member toward the projection hole narrower than the lumen when the tubular portion is moved in the axial direction and the needle portion slides on the guide surface,
    wherein when the needle portion of the tubular member is moved closer to the projection hole of the tubular main body, a deflection of the needle portion is attenuated by the leading surface gradually narrowed to the projection hole.

* * * * *